United States Patent [19]
Basile et al.

[11] Patent Number: 6,042,005
[45] Date of Patent: Mar. 28, 2000

[54] PERSONAL IDENTIFICATION AND PROMOTIONAL SYSTEM USING PERSONAL AND MEDICAL INFORMATION

[76] Inventors: Mark R. Basile, 736 Carlisle Rd., Jericho, N.Y. 11753; Alan H. Weinreb, 135 Redwood Dr., Roslyn, N.Y. 11576

[21] Appl. No.: 08/879,267

[22] Filed: Jun. 20, 1997

[51] Int. Cl.⁷ .................................................. G06K 5/00
[52] U.S. Cl. .......................... 235/382; 235/380; 235/487; 235/492; 283/77
[58] Field of Search .................................. 235/380, 382, 235/487, 492; 902/3, 4; 283/75, 76, 77, 78

[56] References Cited

U.S. PATENT DOCUMENTS

| | | | |
|---|---|---|---|
| 4,709,136 | 11/1987 | Watanabe | 235/379 |
| 4,797,543 | 1/1989 | Watanabe | 235/492 |
| 5,012,229 | 4/1991 | Lennon et al. | 345/1 |
| 5,108,131 | 4/1992 | Nassim | 283/70 |
| 5,171,039 | 12/1992 | Dusek | 283/75 |
| 5,193,855 | 3/1993 | Shamos | 283/117 |
| 5,312,136 | 5/1994 | Capozzola | 283/75 |
| 5,451,763 | 9/1995 | Pickett et al. | 235/492 |
| 5,454,600 | 10/1995 | Floyd | 283/78 |
| 5,597,182 | 1/1997 | Reber et al. | 283/67 |
| 5,675,744 | 10/1997 | Tsujii | 395/203 |
| 5,728,998 | 3/1998 | Novis et al. | 235/380 |
| 5,763,862 | 6/1998 | Jachimowicz et al. | 235/380 |
| 5,765,875 | 6/1998 | Rowley | 283/74 |
| 5,865,470 | 2/1999 | Thompson | 283/70 |

*Primary Examiner*—Donald Hajec
*Assistant Examiner*—Jared J. Fureman
*Attorney, Agent, or Firm*—Collard & Roe, P.C.

[57] ABSTRACT

A personal identification system for children that includes two forms of identification. An identification card carried by the user contains the user's personal and medical information in an electronic medium. The identification card includes photographs of the user and their parent or legal guardian, a unique identification number for the user, and a list of corporate sponsors. The second identification device is to be worn by the user and includes the user's unique identification number and an access telephone number. A user interface enables the users to update their stored personal and medical information.

14 Claims, 2 Drawing Sheets

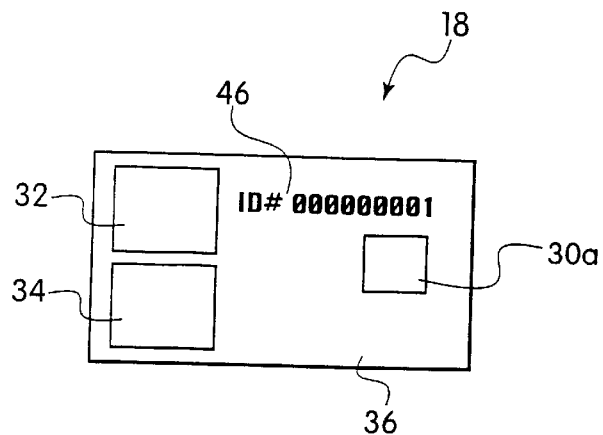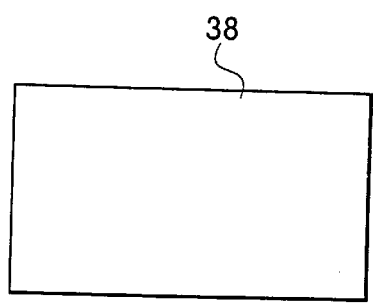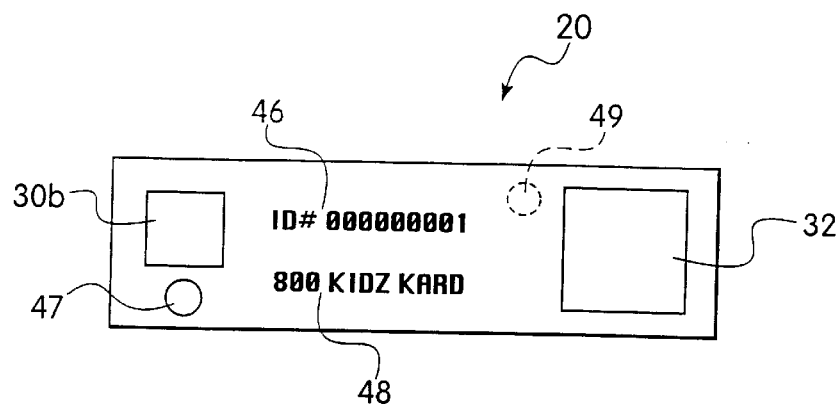

PERSONAL IDENTIFICATION AND PROMOTIONAL SYSTEM USING PERSONAL AND MEDICAL INFORMATION

BACKGROUND OF THE INVENTION

1. Field of the Invention

The present invention relates to identification systems. More particularly, it relates to a children identification system that utilizes interactive smartcard technology and provides the cardholder with corporate discounts at participating stores.

2. The Prior Art

In emergency situations involving children, often times the people reacting to the emergency have insufficient information about the child. The kind of information sought in these situations would be any pertinent medical information for the individual, the child's home address and parents names and numbers, and any other medical or personal information deemed important for purposes of treating this individual.

Many systems have been employed in an effort to provide identification. Among the more well known of these devices is a medical Smartcard™. Generally, medical smartcards do not contain other personal information about the individual and are not used for children.

U.S. Pat. No. 5,012,229 discloses a user wearable personal/medical information device. The device is a bracelet worn on the wrist and contains a ROM (read only memory) for medical information and RAM for personal information. A switch is included for displaying the stored information on a display contained on the wristband. This system provides information about the child, but requires the device to be worn on the users wrist, and does not enable the user to update the medical information stored in the ROM. The user is required to have an additional keyboard control device that is plugged into the wristband in order to update the read/write memory (RAM).

U.S. Pat. No. 5,312,136 discloses an identification tag. The identification tag is designed to be disposed inside the shoe of the person. The ID tag provides medical information about the wearer in the case of an emergency. This device is simply a paper record of a persons medical information attached to the inside of the user's shoe.

U.S. Pat. No. 5,454,600 discloses a personal identification label. The invention discloses an iron-on type patch for childrens clothing that contains a space for receiving the child's fingerprint. The design of the patch is such that the child's fingerprint becomes part of the design, and is camouflaged within the same. The label or patch can be attached to any article of clothing or toy of the child by ironing, sewing, gluing, or any other suitable known means for substantially permanently attaching the label. There is no medical or personal information contained within the label. A special fingerprint recording medium is used on the label in order to assure the permanent disposition of the same.

SUMMARY OF THE INVENTION

The present invention provides an identification and promotional system that increases a child's safety by providing necessary personal information about the child at the specific time and place.

According to the invention, a child's personal information, including medical history, is provided to a manufacturer through a centralized database. The manufacturer encodes the information for the specific individual onto an identification card and tag in the form of an electronic microchip. The card further includes a photograph of the child and/or of their parent or legal guardian. In addition, a unique identification number is also printed on the card.

The manufacturer produces at least one tag that has at least one hole therethrough and can worn by the child. The tag contains a microchip that stores the information, the child's unique identification number, and a telephone number to call for accessing information related to the particular child. The child can wear the tag by threading it through their shoelaces, belt loops, key chains, etc.

An ID access system is provided and includes an instant ID system that enables the pre-authorized operator to access and read the information stored on the microchip, and a security scanner. The security scanner scans the operator identity and confirms them as an authorized user before accessing and displaying the information contained in the microchip. In the preferred embodiment, the security scanner is a bio-metric fingerprint scanning device.

An automated identification system is provided and is used when the microchip contained in the card or tag cannot be read for any reason. The automated identification system is accessed by calling the telephone number on the card or tag, and can provide the caller with the personal information necessary for the present circumstances. Security measures can be implemented to prevent any caller from accessing a child's personal information. Such security measure could be a special access code given to the proper authorities, such as, for example, the police, hospitals, schools, and EMS personnel.

The system includes an online or internet access site for enabling the cardholder and their family to access specific corporate participants to the program and can further enable new users to enroll in the identification program.

The names and logos of the corporate participants are listed on the identification card so that the cardholder and their family may participate in retail promotions provided by the participant. For example, upon presentation of the identification card to a retail outlet of a corporate participant, the cardholder will receive a predetermined discount based on their participation in the identification system program.

It is therefore an object of the present invention to provide a child identification system that can provide instant access to personal and medical information relating to that child in the event of an emergency.

It is another object of the invention to provide a child identification system which includes both an identification card that is carried, and an identification tag that is worn by the child.

It is a further object of the invention to provide a child identification system that can be updated through access to the database or by the child's treating physician.

Yet another object of the invention is to provide a child identification system that provides the card holder with retail discounts.

It is another object of the invention to provide a child identification system that includes an identification card that includes photographs of both the child and their parent or legal guardian or a combination of the same.

It is yet another object of the invention to provide a child identification system that operates efficiently and reliably.

BRIEF DESCRIPTION OF THE DRAWINGS

Other objects and features of the present invention will become apparent from the following detailed description considered in connection with the accompanying drawings which disclose an embodiment of the present invention. It should be understood, however, that the drawings are designed for the purpose of illustration only and not as a definition of the limits of the invention.

In the drawings, wherein similar reference characters denote similar elements throughout the several views:

FIG. 2a is a front plan view of the identification card according to the invention;

FIG. 2b is a back plan view of the identification card according to the invention; and FIG. 3 is a plan view of the identification disc according to the invention.

DETAILED DESCRIPTION OF PREFERRED EMBODIMENTS

Figure 1:
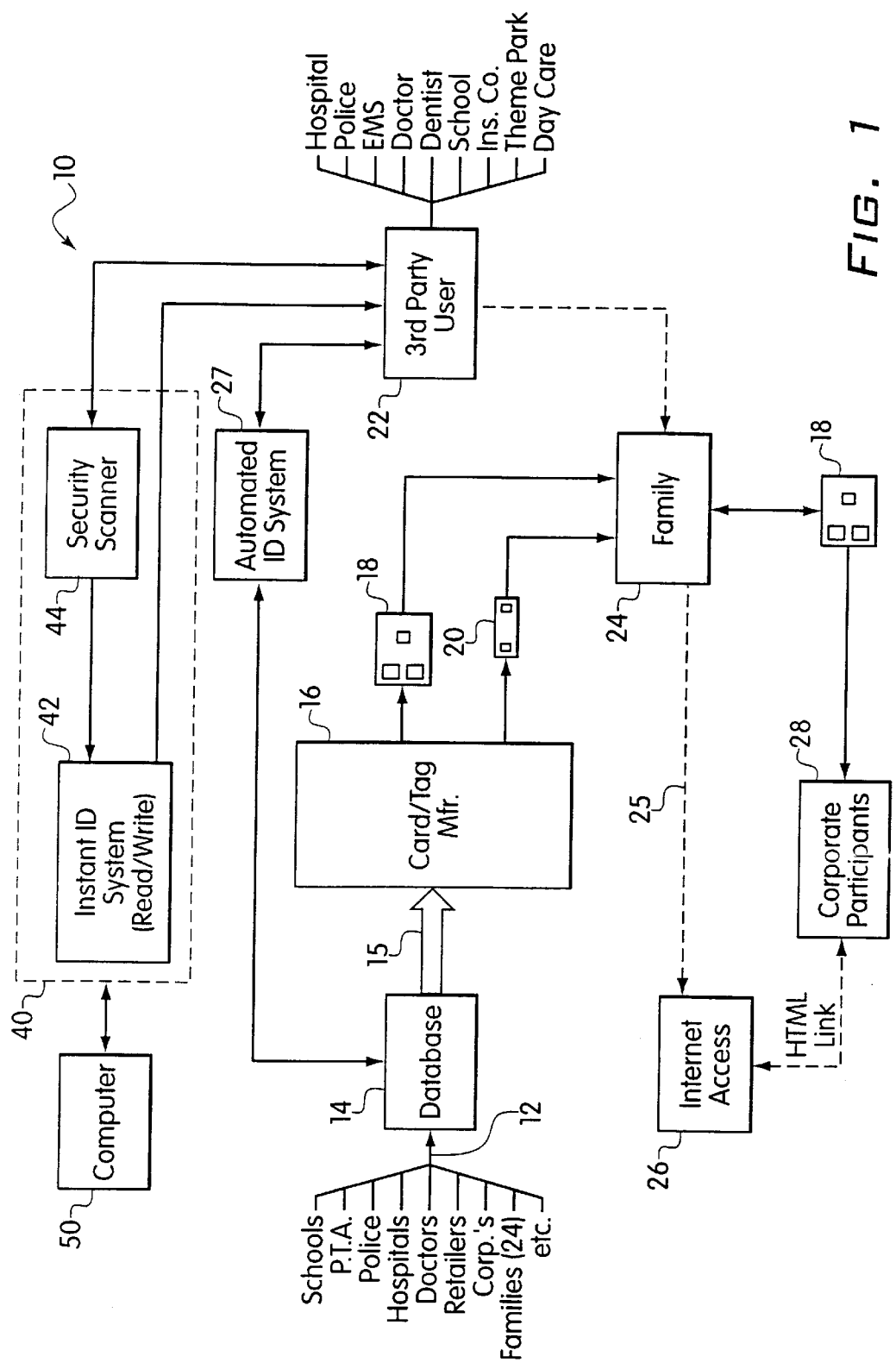
FIG. 1 is a schematic block diagram of the personal identification system according to the invention.

Turning now in detail to the drawings, FIG. 1 shows the identification/promotion system 10 according to the invention. System 10 includes a relational database 14 for receiving and storing identification information for each child participating in the program. A group of organizations such as, for example, schools, P.T.A.'s, police precincts, hospitals, doctors, retail stores, malls, corporations, families, etc. can initiate the enrollment of the children associated with their organization or family by directly providing the child's respective personal and medical information to database 14 through connection 12.

Connection 12 can be any suitable connection to database 14, such as, for example, a hard wired network, a telephone network, and an online computer network using modems. Other suitable methods for transmitting and submitting information to database 14 could be by questionnaires and manual data entry into the database. Database 14 is preferably contained in a general purpose computer (not shown). The general purpose computer will contain software programming that enables the system to operate as described herein.

Once the person's identification information is stored in database 14, a card/tag manufacturer 16 is provided with this information via a secured connection 15. The secured connection 15 prevents loss or tampering with the information being transmitted from database 14 and manufacturer 16. Secured connection 15 can be any suitable known connection that includes security measures for transmitting information. These security measures can include, for example, encryption and de-cryption techniques, complex filtering systems, and any other known method for providing secure transmission of information.

The card/tag manufacturer 16 generates an identification card 18 and at least one identification tag 20 relating to the particular individual. The identification card 18 and tags 20 are given to the family 24 of the individual. Identification card 18 is designed to be carried by the individual, and tag 20 is designed to be worn by the individual. Tags 20 can be worn on shoelaces, key chains, belt loops, or any other article of clothing or device that can be threaded through the hole in tag 20. By providing a removable tag, the individual is not limited as to the particular clothing or shoes they should wear.

FIG. 2a shows identification card 18 as produced by manufacturer 16. The front 36 of card 18 includes a member photo 32 and a parent photo 34. Member photo 32 is a recent photograph of the child who carries the card. Parent photo 34 is a photo of the child's parent or legal guardian. Card 18 includes a unique identification number 46 that is used in conjunction with automated ID system 27 to obtain the child's personal information. The unique identification number 46 can be generated at the time of enrollment in the identification program (12), or can be generated by card/disc manufacturer 16.

Card 18 also includes a memory chip 30 that contains all of the child's personal information in an encoded format. Memory chip 30 can be any suitable known device capable of storing data, such as, for example, ROM, RAM, EPROM's, etc. Memory chip 30 is preferably re-writable so as to enable updating of the information contained therein without requiring a new card or replacement chip.

FIG. 3 shows an example of identification tag 20 according to the invention. Tag 20 is generally rectangular in shape and includes at least one aperture 47 therethrough. Additional apertures 49 could be added to provide more versatility in applying the tag to the childs clothing. Tag 20 can be any desired shape, provided an aperture or means for connecting the same to the child is included. Tag 20 includes a microchip 30b, the child's unique ID number 46 and a special access telephone number 48. In addition, tag 20 can include a picture 32 of the child or individual. Telephone number 48 provides the finder of the child or tag with the ability to contact the automated ID system 27 and retrieve and or report the necessary information about this individual.

When a child, having identification card 18 and/or tag 20 on their person, is involved in an accident, medical trauma, abduction or other life-threatening emergency, a third party user 22 can access all of their personal and medical information by electronically reading microchip 30a or 30b on the card 18 or tag 20, respectively.

An authorized third party user 22 takes the card or tag to their instant access system 40. Instant access system 40 includes an instant ID system 42 and a security scanner 44. The authorized operator must then pass a security check at scanner 44 before instant ID system 42 will read microchip 30a or 30b on the card 18 or tag 20, respectively. Once security scanner 44 has cleared the operators identity, card 20 or tag 18 is read by instant ID system 42 and the child's information is displayed. Some examples of authorizes third party users would be, hospitals, police, EMS, doctors, dentists, schools, insurance companies, theme parks, day care centers, etc.

Instant ID system 42 is a read/write device and will enable the authorized operator to not only read the information contained on microchips 30a and 30b within the card and tag, respectively, it will also enable the operator to instantaneously update the information contained in each respective identification device.

Instant access system 40 is a complete hardware and software package that is installed and setup at the authorized third party location. System 40 would include a general purpose computer 50 or microprocessor control programmed to correlate the functions of the instant ID system 42, security scanner 44, and the third party users 22.

Security scanner 44 is preferably a bio-metric fingerprint scanner.

Instant access system 40 is a complete hardware and software package coupled to a local computer 50 and can be used by hospitals, government agencies, and the police to obtain instant information during potentially life-threatening situations. Computer 50 is local to the particular authorized operators, and is pre-programmed with the necessary control and security parameters for the particular third party user 22.

As an additional security measure, especially for use when microchips 30a and 30b cannot be read, the third party users 22 are provided with their own security code that identifies them as an authority to whom the personal and medical information can be released. This security measure will prevent unauthorized telephone access to user's personal and medical information via the automated ID system 27. Any other suitable known method of preventing unauthorized access to stored user information may also be incorporated into the system.

The information contained in database 14, and microchips 30a and 30b, can be any information deemed necessary for the safety and protection of the child. Examples of this information could be: personal and medical family histories, finger prints, full-page color photo of child, height, age, weight, nicknames, birthmarks or other identifying marks, allergies, medication restrictions, names and addresses of family members, neighbors, doctors, dentists, closest police precinct, medical insurance information, and authorizations to perform emergency surgery, etc. There is no limit to the types of information that can be stored in the system.

Referring to FIG. 1, system 10 includes several features not otherwise associated with personal identification cards. System 10 includes a group of corporate participants 28 who participate in the identification system's program. Corporate participants 28 will provide retail discounts to the individual who presents card 18 at the time of purchase. Through this system the corporate sponsors 28 can increase their retail business.

System 10 includes an internet access site 26 (commonly know as a homepage) for providing the cardholder's family 24 with the ability to access many options and links to other internet sites that are associated with system 10. Once connected, family 24 can access corporate participant's 28 internet sites, enroll new children in the program, and browse other features of the system.

The names and logos of participating corporate sponsors will appear on the back side 38 of card 18. This will provide the cardholder with an indication as to what companies and stores they can receive corporate discounts.

While one embodiment of the present invention have been shown and described, it is to be understood that many changes and modifications may be made thereunto without departing from the spirit and scope of the invention as defined in the appended claims.

What is claimed is:

1. A personal identification system comprising:
   a data storage device adapted to receive and store personal and medical information relating to a user;
   an identification generator connected to said data storage device and adapted to generate identification devices relating to the user;
   a first identification device generated by said identification generator and adapted to be carried by the user, said first identification device being a card having a front and back surface and having a first data storage means adapted to store the user's personal and medical information, said card further comprising:
      a photograph of the user disposed on the front surface;
      a second photograph, of the user's parent or legal guardian disposed on the front surface; and
      a code number adapted to identify the user's personal and medical information contained in said data storage device;
   at least one second identification device generated by said identification generator and adapted to be worn by the user, said second identification device having a second data storage means adapted to store the user's personal and medical information; and
   a data retrieval device adapted to retrieve a user's personal and medical information from said first and second data storage means.

2. The personal identification system according to claim 1, wherein said first data storage means further comprises a programable micro chip embedded into said card.

3. The personal identification system according to claim 1, wherein said second identification device further comprises a tag having at least one aperture adapted to enable the user to connect said tag to an article of clothing, said tag including said unique code and a telephone access number to said data storage device.

4. The personal identification system according to claim 3, wherein said second data storage means further comprises a programmable micro chip embedded into said tag.

5. The personal identification system according to claim 1, wherein said data retrieval device further comprises an automated identification system adapted to receive inquiries relating to said first and second identification devices and provide responses to those inquiries.

6. The personal identification system according to claim 1, wherein said data retrieval device further comprises an instant ID access system adapted to read and display the stored medical and personal information contained within said first and second data storage means.

7. The personal identification system according to claim 6, wherein said instant ID access system comprises;
   an instant ID system adapted to read the information contained in said first and second data storage means;
   a security scanner connected to said instant ID system and adapted to check the authorized user's identity prior to accessing the information contained in the said first and second data storage means; and
   a general purpose computer connected to said instant ID access system and being programmed to operate said instant ID system and said security scanner.

8. The personal identification system according to claim 1, further comprising an internet access site, said access site comprising:
   a first link adapted to enable a user to create a new account; and
   a plurality of links to corporate participants of the personal identification system.

9. The personal identification system according to claim 1, wherein said back surface of said card includes a plurality of names and logos of corporate sponsors, wherein the corporate sponsors provide retail discounts to the user of said card.

10. A method for providing personal identification comprising the steps of:
   receiving a user's personal and medical information;
   storing the received user information;
   manufacturing a first identification device based on the stored user information, the first identification device being carried by the user, and comprising the steps of:
      assigning a unique identification number to the user;
      printing the assigned user identification number on the first identification device;
      storing the user information on the first identification device, printing a photograph of the user on the identification device, and printing a photograph of the user's parent or legal guardian on the identification device;

manufacturing a second identification device based on the stored user information, the second identification device being worn by the user; and providing selective access to the stored user information for providing emergency services related to the particular user.

11. The method according to claim 10, wherein said step of manufacturing a second identification device further comprises the steps of:

assigning a unique identification number to the user;

storing the user information on said second identification device;

printing the assigned identification number on the second identification device; and printing a telephone number on the second identification device.

12. The method according to claim 10, wherein said step of providing selective access to the stored user information includes providing access codes to specific authorities for preventing unauthorized access to the stored user information.

13. The method according to claim 10, further comprising the steps of:

providing a first user interface for enabling current users to access and update their stored user information;

providing a second user interface for enabling new users to enroll in the program and provide their user information; and providing retail store discounts to the users based on their participation in the identification program.

14. The method according to claim 10, wherein said steps of providing first and second user interfaces comprises the step of establishing an online access site that is accessible from the user's home or office computer.

* * * * *